United States Patent [19]

Stahly

[11] Patent Number: 4,990,699

[45] Date of Patent: Feb. 5, 1991

[54] PERFLUOROALKYLATION PROCESS

[75] Inventor: G. Patrick Stahly, Baton Rouge, La.

[73] Assignee: Ethyl Corporation, Richmond, Va.

[21] Appl. No.: 258,650

[22] Filed: Oct. 17, 1988

[51] Int. Cl.$^5$ ............................................ C07C 205/06
[52] U.S. Cl. .................... 568/933; 568/932; 568/927; 568/936; 570/146
[58] Field of Search .................. 568/932, 933, 936; 570/142

[56] References Cited

U.S. PATENT DOCUMENTS 3,507,924  4/1970  Hakansson et al. .
4,188,274  2/1980  Fields .................................. 568/936
4,467,125  8/1984  Chupp et al. ....................... 568/936

OTHER PUBLICATIONS

Carr, Gillian E., "Sodium Perfluoroalkane Carboxylates as Sources of Perfluoroalkyl Groups", *Journal Chemical Society*, Perkins Trans. (1988), pp. 921–925.
Matsui et al., "A convenient Trifluoromethylation of Aromatic Halides with Sodium Trifluoroacetate", *Chemistry Letters*, (1981), pp. 1719–1720.
Krishnamurthy, S., "Acetyl Hypofluorite as a Taming Carrier of Elemental Fluorine for Novel Electrophilic Fluorination of Activated Rings", *Journal of Organic Chemistry*, 46 (1981), pp. 4629–4631.
Haszeldine, R. N., "Perfluoroalkyl Grignard and Grignard-Type Reagent, Part IV, Trifluoromethylmagnesium Iodide", *Journal of Chemistry Society*, (1954) pp. 1273–1279.
Hine, Jack, *Physical Organic Chemistry*, New York: McGraw-Hill Book Company, Inc., 1962.
McBee et al., "Preparation and Reactions of Perfluoroalkyllithiums", *Journal of American Chemical Society*, vol. 76 (1953), 474–478.
Wiemers et al., "Pregeneration, Spectroscopic Detection, and Chemical Reactivity of (Trifluoromethyl) Copper, and Elusive and Complex Species", *Journal America Chemical Society*, 108 (1986), 832–834.
McBee, et al. "A New Synthesis of Perfluoroalkyl Magnesium Halides", *Journal of Organic Chemistry*, 28 (1963), 1131–1133.
Bergman, Elliot, "Decorboxylation of Perfluoracid Esters", *Journal of Organic Chemistry*, 23 (1958), 476–477.
Strauss, Michael, "Anionic Sigma Complexes", *Chemical Reviews*, vol 70, No. 6, (1970), 667–711.
*Advanced Organic Chemistry: Reactions, Mechanisms, and Structure*, 3rd edition, Jerry March, N.Y., 1985, pp. 556–557.

Primary Examiner—Robert L. Stoll
Assistant Examiner—Valerie Fee
Attorney, Agent, or Firm—Richard J. Hammond; John F. Sieberth

[57] ABSTRACT

Despite the instabity of perfluoralkyl anions, it is possible to perfluoroalkylate aromatic compounds if appropriately substituted by suitable electronegative substituents (e.g., nitro, trifluoromethylsulfonyl, etc.). Thus a novel Meisenheimer complex is formed by thermally decomposing a salt of a perfluoroalkanoic acid in the presence of an aromatic compound such as 1,3,5-trinitrobenzene. Oxidation with organic hypochlorite yields the corresponding perfluoroalkylated aromatic compound.

19 Claims, No Drawings

PERFLUOROALKYLATION PROCESS

TECHNICAL FIELD

This invention relates to perfluoroalkylation of aromatic compounds, viz., certain benzenoid compounds which contain strong electron withdrawing groups.

BACKGROUND

Perfluoroalkyl anions are extremely unstable. Early attempts to generate nucleophilic metal trifluoromethide compounds were unsuccessful. See Haszeldine, *J. Chem. Soc.*, 1954, 1273; Pierce et al, *J. Am. Chem. Soc.*, 1954, 76, 474; Bergman, *J. Org. Chem.*, 1958, 23, 476; McBee et al, *J. Org. Chem.*, 1963, 28, 1131. Presumably, this is due to the rapid dissociation of $CF_3$ into $CF_2$ and $F^-$ (Hine, *Physical Organic Chemistry*, McGraw-Hill, New York, 1962, p 486). More recently, reports have appeared describing trifluoromethylcopper ($CF_3Cu$), which exhibits nucleophilic character—see Wiemers et al, *J. Am. Chem. Soc.*, 1986, 108, 832 and references cited therein; and McClinton et al, *Chem. Commun.*, 1988, 638. This reagent will displace halogen atoms from aromatic rings. One method of $CF_3Cu$ generation is the decomposition of metal trifluoroacetates in the presence of copper (I) iodide (Matsui et al, *Chem. Letters*, 1981, 1719; Carr et al, *J. Chem. Soc., Perkin Trans.* 2, 1988, 921).

THE INVENTION

This invention involves, inter alia, the discovery that it is possible to perfluoroalkylate aromatic compounds by a formal displacement of a hydrogen atom from the ring, if the aromatic compound is appropriately substituted by suitable electronegative substituents. More particularly, a Meisenheimer complex can be formed by thermally decomposing a salt of a perfluoroalkanoic acid in the presence of an aromatic compound of the formula

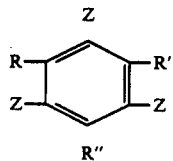 (I)

where Z is a nitro group or other electron withdrawing group having an electronegatively comparable to or greater than that of the nitro group; and R, R' and R" are, independently, hydrogen, hydrocarbyl, hydrocarbyloxy or esterified carboxy substituents, at least one of R, R' and R" being a hydrogen atom. The Meisenheimer complex in turn can be oxidized to form a compound of formula (I) above in which an original hydrogen atom on the ring (R, R' or R") is replaced by a perfluoroalkyl group.

These reactions are illustrated by the trifluoromethylation of 1,3,5-trinitrobenzene by thermal decomposition of potassium trifluoroacetate in the presence of 1,3,5-trinitrobenzene, and the oxidation of the resultant Meisenheimer complex with tert-butyl-hypochlorite:

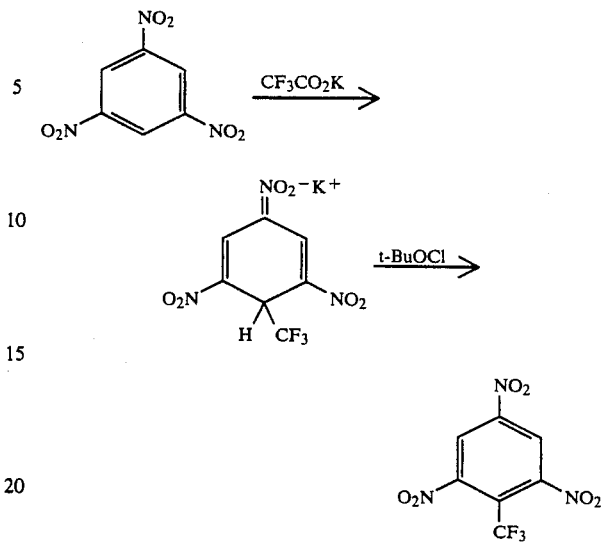

The Meisenheimer complexes of the type formed pursuant to this invention are new and useful compositions, and may be represented by the general formula:

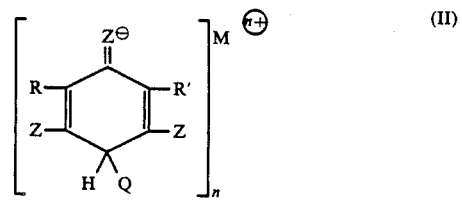 (II)

where Z is a nitro group or other electron withdrawing group that has an electronegativity comparable to or greater than that of the nitro group; Q is a perfluoroalkyl group; R and R' are, independently, hydrogen, hydrocarbyl, hydrocarbyloxy or esterified carboxy substituents, M is a metallic cation, and n is a number corresponding to the valence of M. A feature of this invention is that the trinitro complexes on controlled oxidation produce 1-perfluoroalkyl-2,4,6-trinitrobenzenes and derivatives thereof, compounds which heretofore required use of expensive starting materials and more complicated processing. For example, the only known route to 1-trifluoromethyl-2,4,6-trinitrobenzene, a compound shown to have superior heat stability, impact stability, and explosive power compared to trinitrotoluene (TNT), was quite laborious, involving nitration, chlorination, and reduction of 3-trifluoromethylphenol. See U.S. Pat. No. 3,417,153.

The thermal decomposition step is preferably conducted in, a dipolar aprotic solvent system such as N,N-dimethylformamide, N,N-dimethylacetamide, dimethylsulfoxide, N-methylpyrrolidinone, hexamethylphosphoramide, acetonitrile, nitrobenzene, sulfolane, and the like, although other less polar aprotic solvents may be found suitable. It is convenient to conduct the oxidation in the same solvent medium as used in the initial reaction (although other solvents may be used if desired) and for this reason it is preferred to utilize in the overall process a dipolar aprotic solvent that is not readily oxidized by the oxidant used in the second step. The N,N-dilower alkyl formamides and acetamides are thus among the preferred reaction media for use in both steps of the process.

Various perfluoroalkanoic acid salts that undergo the desired nucleophilic reaction to form a Meisenheimer complex may be used in the process These include the sodium, potassium, cesium, calcium, magnesium, barium, aluminum, silver, mercury (II), zinc, thallic (III), etc., salts of the perfluoroalkanoic acids such as trifluoroacetic, pentafluoropropionic, perfluorobutanoic, perfluoropentanoic, perfluorohexanoic, perfluorooctanoic, and like acids, whether linear or branched chain in character. The potassium salts of the $C_1$ to $C_6$ perfluoroalkanoic acids are preferred.

The substituted aromatic compounds that may be used in the process include 1,3,5-trinitrobenzene, 2,4,6-trinitrotoluene, 2,4,6-trinitro-m-xylene, 3-tert-butyl-2,4,6-trinitrotoluene, 2,4,6-trinitroanisole, methyl 2,4,6-trititrobenzoate, ethyl 2,4,6-trinitrobenzoate, butyl 2,4,6-trinitrobenzoate, 2,4,6-trinitrodiphenyl ether, 2,4,6-trinitrophenyl ethyl ether, 1,3,5-tris(trifluoromethylsulfonyl)benzene, 2,4,6-tris(trifluoromethylsulfonyl)toluene, 2,4,6-tris(trifluoromethylsulfonyl)-m-xylene, and the like.

The reaction between the perfluoroalkanoic acid salt and the substituted aromatic compound should be conducted at a temperature at which the salt thermally dissociates to form the Meisenheimer complex with the substituted aromatic compound. Typically this temperature will be above about 100° C., although any temperature at which the desired reaction takes place can be used.

Suitable oxidants for use in the second step of the process include organic hypochlorites, organic hypobromites, chlorine, bromine, and similar materials. The oxidations are conveniently performed at room (ambient) temperatures, although the system may be heated or cooled if desired.

The following examples are illustrative of this invention.

EXAMPLE 1

A mixture of potassium trifluoroacetate (210 mg, 1.4 mmol and 1,3,5-trinitrobenzene (100 mg, 0.47 mmol) in one mL of N,N-dimethylformamide (DMF) or in one mL of dimethylsulfoxide (DMSO) was heated at 150° C. for one hour. A deep red solution of a Meisenheimer complex of formula (II) above (Z=nitro; Q=trifluoromethyl; R and R'=H; M=K; and n=1) was obtained. The structure of the complex was verified by NMR spectroscopy. Oxidation of a DMF solution of this complex by dropwise addition of tert-butylhypochlorite until the red color disappeared (about seven drops) followed by aqueous workup (10 mL of 1M HCl, extracted with three portions of diethyl ether afforded an oil. This was purified by preparative thin layer chromatography (one 2 mm silica gel plate eluted with 50% petroleum ether/50% dichloromethane) to give 53 mg (40% yield) of 1-trifluoromethyl2,4,6-trinitrobenzene.

EXAMPLE 2

Using the procedure of Example 1, potassium pentafluoropropionate was reacted with 1,3,5-trinitrobenzene in DMF at 150° C. to form a Meisenheimer complex of formula (II) above wherein Z=nitro; Q=pentafluoroethyl; R and R'=H; M=K; and n=1). Oxidation with tert-butylhypochlorite and purification by preparative thin layer chromatography gave 1-pentafluoroethyl-2,4,6-trinitrobenzene in 65% yield.

The foregoing disclosure has been presented for purposes of illustration and not limitation. As can readily be appreciated by those skilled in the art, this invention is susceptible to considerable variation in its practice within the spirit and scope of the ensuing claims.

What is claimed is:

1. A process which comprises thermally decomposing a salt of a perfluoroalkanoic acid in the presence of an aromatic compound of the formula

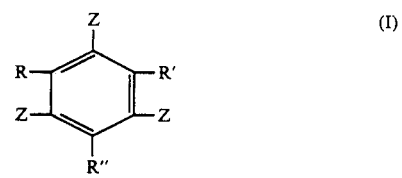

where Z is a nitro or a trifluoromethylsulfonyl group and R, R' and R" are, independently, hydrogen, $C_1$ to $C_4$ linear or branched alkyl, methoxy, phenoxy, ethoxy or the group —C(O)OR$_2$ where R$_2$ is $C_1$ to $C_4$ linear or branched alkyl at least one of R, R' and R" being a hydrogen atom; such that a perfluoroalkylated Meisenheimer complex of the formula

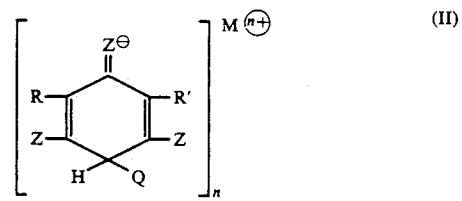

where Q is a perfluoroalkyl group; M is a metallic cation that is sodium, potassium, cesium, calcium, magnesium, barium, aluminum, silver, mercury (II), zinc, or thallium (III); n is a number corresponding to the valence of M and Z, R and R' are as previously defined, is formed therefrom.

2. A process of claim 1 wherein Z is nitro.

3. A process of claim 1 conducted in a dipolar aprotic solvent reaction medium.

4. A process of claim 3 wherein Z is nitro.

5. A process of claim 3 wherein the aromatic compound is 1,3,5-trinitrobenzene.

6. A process of claim 3 wherein the perfluoroalkanoic acid salt is an alkali metal salt.

7. A process of claim 2 wherein the perfluoroalkanoic acid salt is a potassium salt.

8. A process of claim 3 wherein the perfluoroalkanoic acid salt is a salt of trifluoroacetic acid or pentafluoropropionic acid.

9. A process of claim 3 wherein the perfluoroalkanoic acid salt is potassium trifluoroacetate or potassium pentafluoropropionate.

10. A process of claim 9 wherein the aromatic compound is 1,3,5-trinitrobenzene.

11. A process of claim 1 conducted in a dipolar aprotic solvent reaction medium.

12. A process of claim 11 wherein Z is nitro.

13. A process of claim 11 wherein the aromatic compound is 1,3,5-trinitrobenzene.

14. A process of claim 11 wherein the perfluoroalkanoic acid salt is an alkali metal salt.

15. A process of claim 11 wherein the perfluoroalkanoic acid salt is a potassium salt.

16. A process of claim 12 wherein the perfluoroalkanoic acid salt is a salt of trifluoroacetic acid or pentafluoropropionic acid.

17. A process of claim 11 wherein the perfluoroalkanoic acid salt is potassium trifluoroacetate or potassium pentafluoropropionate.

18. A process of claim 17 wherein the aromatic compound 1,3,5-trinitrobenzene.

19. A process which comprises
(a) thermally decomposing a salt of a perfluoroalkanoic acid in the present of an aromatic compound of the formula

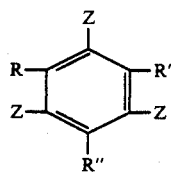

where Z is a nitro or a trifluoromethylsulfonyl group; and R, R' and R'' are, independently, hydrogen, $C_1$ to $C_4$ linear or branched alkyl, methoxy, phenoxy, ethoxy or the group —C(O)OR$_2$ where R$_2$ is $C_1$ and $C_4$ linear or branched alkyl; at least one of R, R' and R'' being a hydrogen atom; such that a perfluoroalkylated Meisenheimer complex of the formula

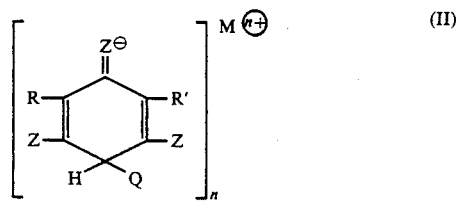

where Q is a perfluoroalkyl group; M is a metallic cation that is sodium, potassium, cesium, calcium, magnesium, barium, aluminum, silver, mercury (II), zinc, or thallium (III); n is a number corresponding to the valence of M and Z, R and R' are as previously defined, is formed therefrom; and (b) oxidizing such complex to produce a compound of formula (I) in which an original hydrogen atom on the ring is replaced by a perfluoroalkyl group.

* * * * *

UNITED STATES PATENT AND TRADEMARK OFFICE
CERTIFICATE OF CORRECTION

PATENT NO. : 4,990,699

DATED : February 5, 1991

INVENTOR(S) : G. Patrick Stahly

It is certified that error appears in the above-identified patent and that said Letters Patent is hereby corrected as shown below:

Column 4, line 50, reads "claim 2" and should read --claim 3--.

Column 4, line 62, reads "claim 12" and should read --claim 11--.

Column 5, line 1, reads "claim 12" and should read --claim 11--.

Signed and Sealed this

First Day of December, 1992

Attest:

DOUGLAS B. COMER

*Attesting Officer*  Acting Commissioner of Patents and Trademarks